United States Patent
Demetriou

(10) Patent No.: US 12,246,152 B2
(45) Date of Patent: Mar. 11, 2025

(54) APPARATUS FOR MEASURING PRESSURE WITHIN A SHUNT

(71) Applicant: Vias Demetriou, Newcastle-upon-Tyne (GB)

(72) Inventor: Vias Demetriou, Newcastle-upon-Tyne (GB)

(*) Notice: Subject to any disclaimer, the term of this patent is extended or adjusted under 35 U.S.C. 154(b) by 1190 days.

(21) Appl. No.: 16/316,284

(22) PCT Filed: Jul. 7, 2017

(86) PCT No.: PCT/GB2017/051999
§ 371 (c)(1),
(2) Date: Jan. 8, 2019

(87) PCT Pub. No.: WO2018/007825
PCT Pub. Date: Jan. 11, 2018

(65) Prior Publication Data
US 2020/0179664 A1    Jun. 11, 2020

(30) Foreign Application Priority Data
Jul. 8, 2016 (GB) .................................... 1611935

(51) Int. Cl.
*A61M 27/00* (2006.01)
*A61B 5/00* (2006.01)
*A61B 5/03* (2006.01)

(52) U.S. Cl.
CPC ........... *A61M 27/006* (2013.01); *A61B 5/031* (2013.01); *A61B 5/032* (2013.01); *A61B 5/6852* (2013.01); *A61M 2205/32* (2013.01)

(58) Field of Classification Search
CPC ....... A61B 5/031; A61B 5/032; A61B 5/6852; A61M 27/006; A61M 2205/32
See application file for complete search history.

(56) References Cited

U.S. PATENT DOCUMENTS

| 3,977,391 | A | 8/1976 | Fleischmann |
| 4,172,449 | A | 10/1979 | Bruner et al. |
| 4,627,443 | A | 12/1986 | Chubbuck et al. |
| 5,935,084 | A * | 8/1999 | Southworth ........... A61B 5/037 600/561 |
| 7,383,736 | B2 * | 6/2008 | Esnouf ................... G01L 7/063 73/716 |

(Continued)

FOREIGN PATENT DOCUMENTS

EP    0904728 A2    3/1999

OTHER PUBLICATIONS

International Search Report and Written Opinion dated Nov. 6, 2017, for corresponding PCT Application No. PCT/GB2017/051999.

*Primary Examiner* — Alex M Valvis
*Assistant Examiner* — Nidhi N Patel
(74) *Attorney, Agent, or Firm* — Kinney & Lange, P.A.

(57) ABSTRACT

An apparatus for measuring pressure of fluid in a shunt includes a distensible member arranged adjacent to a graduated scale. The shunt includes a shunt valve and the apparatus is attachable to, or incorporated into the shunt at a location either at the shunt valve or upstream of the shunt valve. Both the distensible member and the scale include radiopaque markers. The fluid in the shunt acts directly on the distensible member and the distensible member is distensible in the direction of the scale.

11 Claims, 6 Drawing Sheets

(56) References Cited

U.S. PATENT DOCUMENTS

2008/0249458 A1* 10/2008 Yamasaki ........... A61M 27/006
  604/8
2016/0007851 A1   1/2016 Araci et al.

* cited by examiner

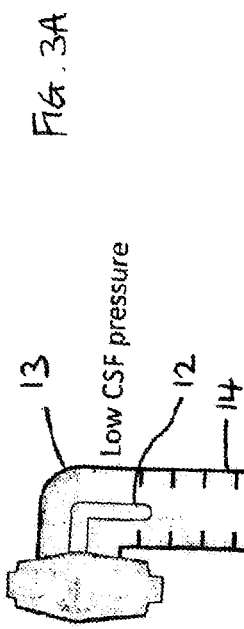
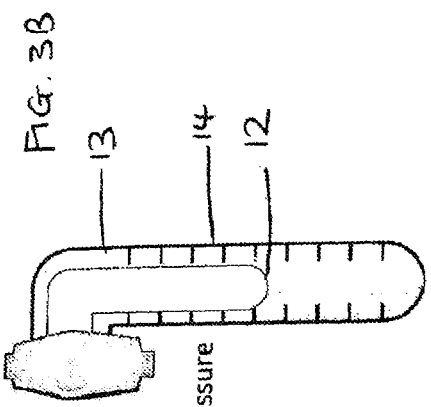
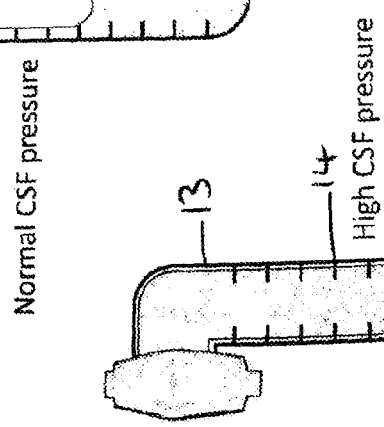
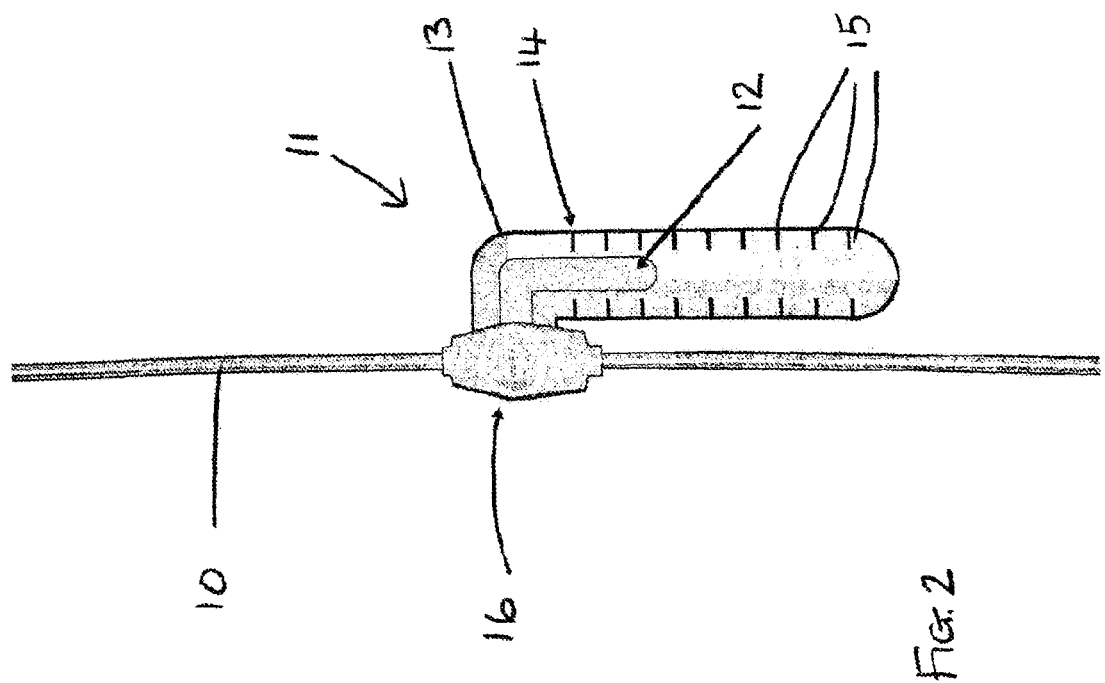

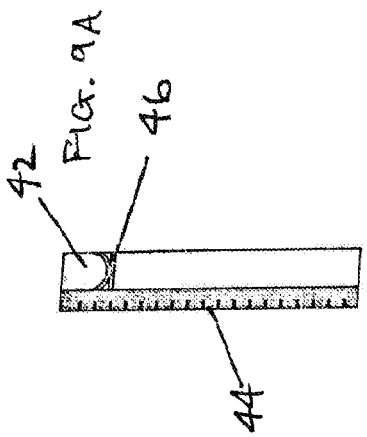
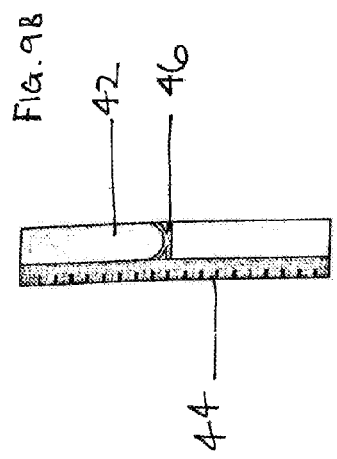
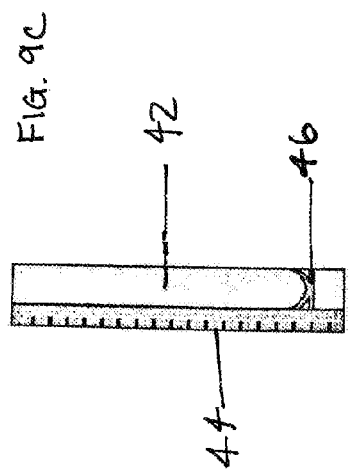
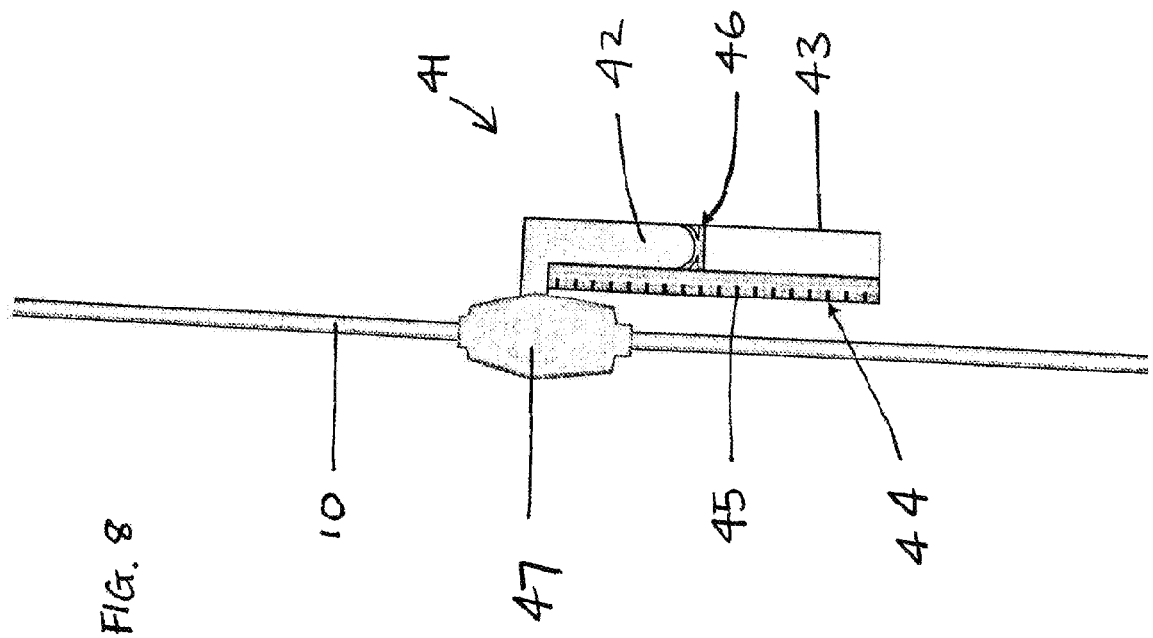

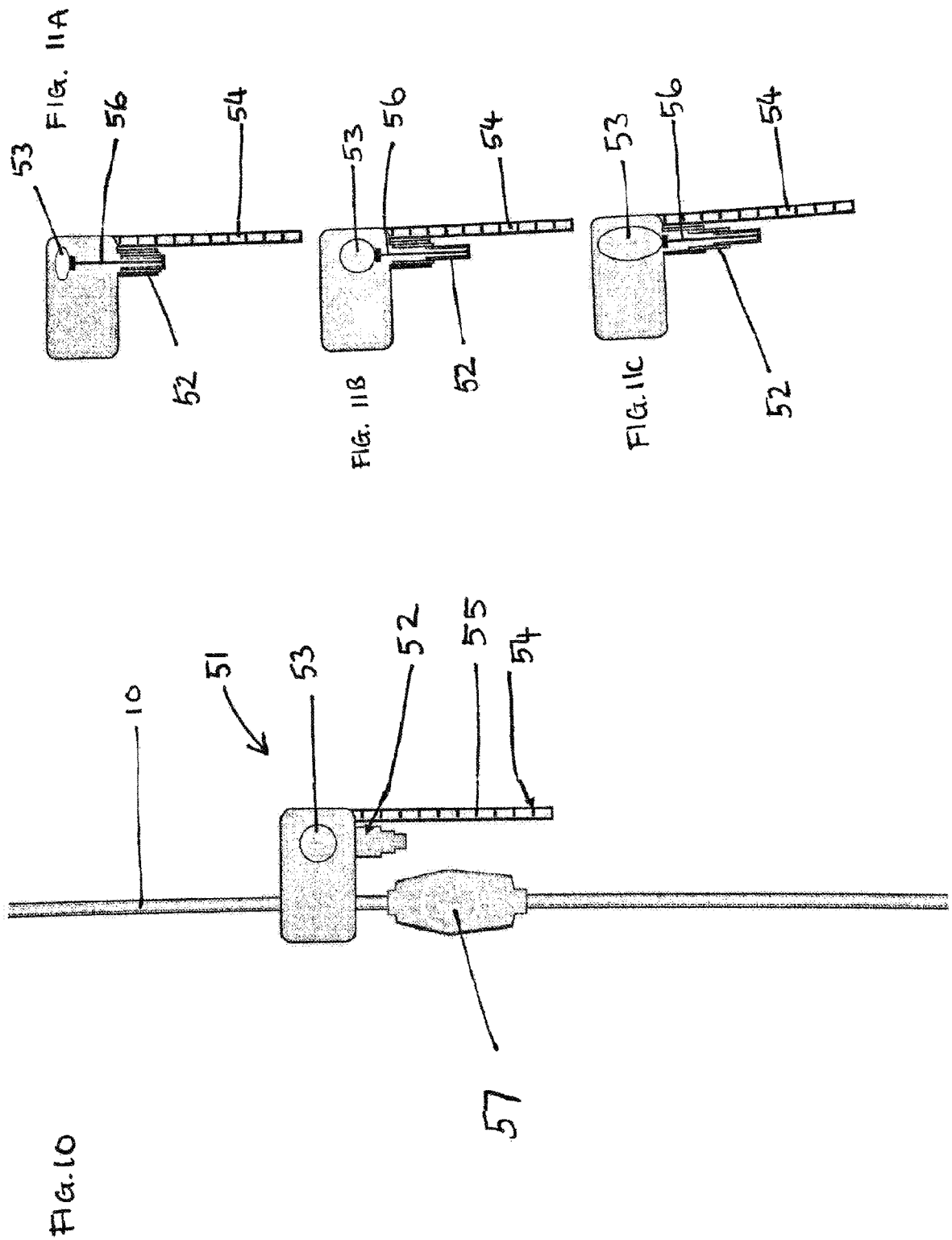

APPARATUS FOR MEASURING PRESSURE WITHIN A SHUNT

CROSS-REFERENCE TO RELATED APPLICATION(S)

This application is the national phase of PCT Application No. PCT/GB2017/051999 filed on Jul. 7, 2017, which in turn claims priority to British Application No. 1611935.6 filed on Jul. 8, 2016. The entire contents of both of these applications are incorporated by reference herein.

TECHNICAL FIELD

The present disclosure relates to apparatus for measuring fluid pressure within a shunt, and in particular to apparatus for measuring cerebrospinal fluid pressure in cerebral shunts.

BACKGROUND

Cerebrospinal fluid (CSF) is a fluid which protects the brain and spine. It is produced in spaces within the brain called ventricles. CSF circulates within the ventricles, then out through channels into spaces between the coverings of the brain called the meninges, from where it is absorbed back into blood vessels. Imbalances in the production, flow and reabsorption of CSF contributes to development of a condition called hydrocephalus. Hydrocephalus is a condition in which a patient accumulates excessive CSF within the ventricles. Untreated, hydrocephalus leads to increased intracranial pressure inside the skull which is harmful to the patient.

As illustrated in FIG. 1, treatment of hydrocephalus usually involves the insertion of a ventricular shunt into the lateral ventricles 1 to allow drainage of excess fluid away from the ventricles 1 and into another body cavity 2, from where it can be reabsorbed. A ventricular shunt comprises a ventricular catheter 3 inserted into a ventricle 1, a shunt valve 4, and a distal catheter 5. All of the components of the ventricular shunt are implanted under the skin. Ventricular shunts typically drain CSF into the peritoneal cavity in the abdomen of the patient. Such shunts are called ventriculoperitoneal shunts or VPS. Shunt systems typically include valve mechanisms 4 that allow fluid to flow only once the fluid pressure reaches a certain threshold value. The valve mechanisms are usually magnetic and can be adjusted non-invasively using a magnet outside the body.

Ventriculoperitoneal shunting is not always straightforward, and patients can often present with symptoms of over-drainage, such as low pressure headaches, or under-drainage of CSF with dangerous symptoms of high intracranial pressure. Patients presenting with symptoms of either over- or under-drainage need to have the pressure of the fluid in the shunt measured somehow. Typically these patients are required to undergo a CT scan to evaluate the size of the ventricles compared to previous scans. Alternatively, or additionally, patients are required to undergo an invasive procedure whereby the shunt is 'tapped' by piercing the shunt with a needle and connecting the needle to a manometer to measure the pressure of the fluid within it. This technique is an effective diagnostic technique but is highly invasive, uncomfortable for the patients, and carries a risk of introducing shunt infection. Shunt infection can be life threatening, and invariably necessitates the removal of the shunt. Once the over- or under-drainage of CSF is diagnosed the valve in the shunt can be adjusted from the outside of the body using a magnetic tool. Further CT scans and/or shunt tapping is required after a few hours to confirm that the valve adjustment has worked correctly. CT scans of the skull expose the patient to much more radiation than a standard X-ray, typically 20 times more than a chest X-ray. Unnecessary exposure to radiation is especially of concern in children whose tissues have a greater sensitivity to radiation.

EP0904728 describes an implantable pressure measurement device which includes a sealed flexible member filled with a predetermined amount of fluid. This devices measures CSF pressure indirectly. A change in CSF pressure external to the devices causes expansion or contraction of the fluid in the flexible member. The expansion or contraction of the fluid moved the flexible member along a scale. This device measures the change in volume of the fluid and calculates the CSF pressure from this measurement. EP0904728 covers the use of this device in conjunction with ventriculoperitoneal shunts. Use of a secondary fluid to determine the CSF pressure is a potential source of error, and there is always a risk of leakage of the secondary fluid.

It would therefore be desirable to provide an apparatus which allows direct measurement of CSF pressure within a shunt without recourse to lengthy and/or invasive procedures.

SUMMARY

According to a first aspect of the disclosure there is provided an apparatus for measuring pressure of fluid in a shunt, the apparatus comprising a distensible member arranged adjacent to a graduated scale and both the distensible member and the scale comprise radiopaque markers, wherein the fluid in the shunt acts directly on distensible member and the distensible member is distensible in the direction of the scale, and wherein the apparatus is attachable to, or incorporated into, the shunt at a location either at or upstream of a shunt valve forming part of the shunt.

Fluid within the shunt acts directly on the distensible member, causing it to distend. Fluid at higher pressure causes the distensible member to distend to a larger extent. The radiopaque markers allow the extent of distension of the distensible member to be assessed using a standard X-ray image.

Preferably the distensible member is fabricated from a radiopaque material, that is a material that is opaque to X-rays and therefore is visible on an X-ray image.

Preferably the distensible member comprises distensible tubing. The distensible member may be fabricated from silicone rubber.

Preferably the fluid is cerebrospinal fluid (CSF).

Preferably the shunt is a ventricular shunt. The apparatus may be attachable to a ventricular catheter forming part of a ventricular shunt.

The graduated scale may be located directly on the ventricular catheter of the cerebral shunt. Alternatively, the graduated scale may form a separate part of the apparatus.

The apparatus of the disclosure allows measurement of CSF pressure within a shunt without recourse to lengthy and/or invasive procedures such as CT scans and shunt tapping procedures. A simple X-ray image is all that is required to assess the CSF pressure within the shunt. The exposure of the patient to radiation is also vastly reduced through the use of X-ray imaging rather than CT scans. In addition, the apparatus of the disclosure allows a direct measurement of fluid pressure in the shunt, such an arrangement is more reliable and there is no risk of leakage of any secondary, pressure transmitting, fluids.

BRIEF DESCRIPTION OF THE DRAWINGS

In the drawings, which illustrate a preferred embodiment of the apparatus of the disclosure, and are by way of example:

FIG. 2 is a schematic view of an apparatus according to a first embodiment of the disclosure;

FIG. 3a is a schematic view of the apparatus of FIG. 2 measuring low pressure CSF;

FIG. 3b is a schematic view of the apparatus of FIG. 2 measuring normal pressure CSF;

FIG. 3c is a schematic view of the apparatus of FIG. 2 measuring high pressure CSF;

FIG. 8 is a schematic view of an apparatus according to a fourth embodiment of the disclosure;

FIG. 9a is a schematic view of the apparatus of FIG. 8 measuring low pressure CSF;

FIG. 9b is a schematic view of the apparatus of FIG. 8 measuring normal pressure CSF;

FIG. 9c is a schematic view of the apparatus of FIG. 8 measuring high pressure CSF;

FIG. 10 is a schematic view of an apparatus according to a fifth embodiment of the disclosure;

FIG. 11a is a schematic view of the apparatus of FIG. 10 measuring low pressure CSF;

FIG. 11b is a schematic view of the apparatus of FIG. 10 measuring normal pressure CSF; and FIG. 11c is a schematic view of the apparatus of FIG. 10 measuring high pressure CSF;

DETAILED DESCRIPTION

Figure 1:
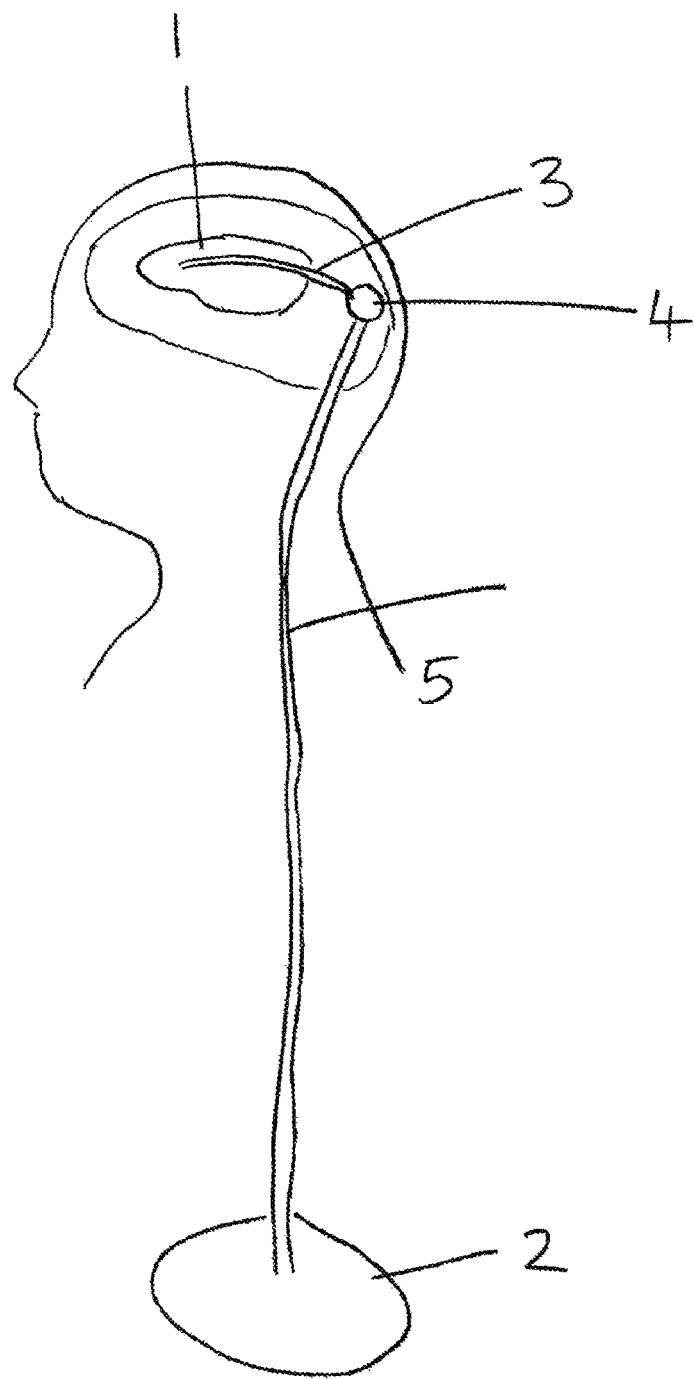
FIG. 1 is a schematic view of a prior art cerebral shunt.

Referring to FIGS. 2 and 3a, 3b and 3c, FIG. 2 illustrates a ventricular catheter 10, including a shunt valve 16 which forms part of a ventricular shunt. Apparatus 11 for measuring pressure of CSF fluid within the shunt is connected to the ventricular catheter 10 at the shunt valve 16. The apparatus 11 may be incorporated into the shunt valve 16 as a single unit. The apparatus 11 includes a distensible member 12 which is located within an outer container 13. The outer container 13 is provided with a scale 14 marked with radiopaque markers 15. The distensible member 13 is made from or coated with a radiopaque material and the outer container 14 is transparent to X-rays, so that the length of the distensible member 12 with respect to the scale 14 can be assessed from an X-ray image of the apparatus 11. To assess the CSF pressure an X-ray image of the apparatus 11 is obtained to enable medical professionals to determine the length of the distensible member 12 with respect to the scale 14 and hence determine the CSF pressure in the patient's shunt. FIG. 3a illustrates an apparatus 11 taking a measurement in a patient with low CSF pressure. The distensible member 12 extends only a small amount along the scale 14. FIG. 3b illustrates an apparatus 11 taking a measurement in a patient with normal CSF pressure. The distensible member 12 extends further along the scale 14. FIG. 3c illustrates an apparatus 11 taking a measurement in a patient with high CSF pressure. The distensible member 12 extends much further along the scale 14.

Figure 5A:
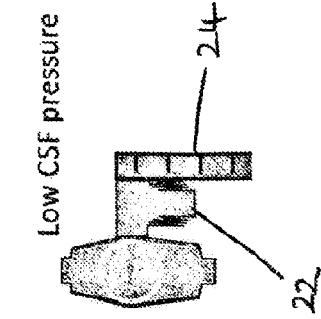
FIG. 5a is a schematic view of the apparatus of FIG. 4 measuring low pressure CSF.
Figure 5C:
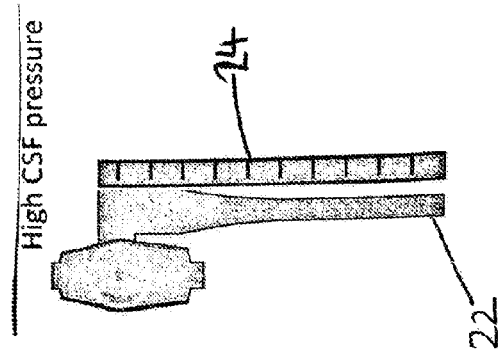
FIG. 5c is a schematic view of the apparatus of FIG. 4 measuring high pressure CSF.
Figure 5B:
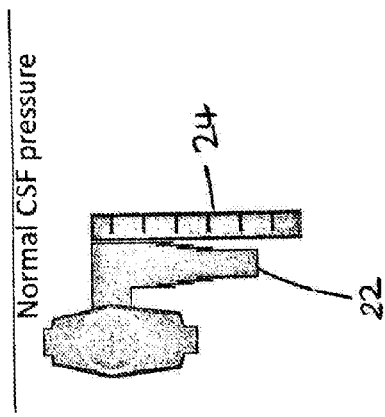
FIG. 5b is a schematic view of the apparatus of FIG. 4 measuring normal pressure CSF.
Figure 4:
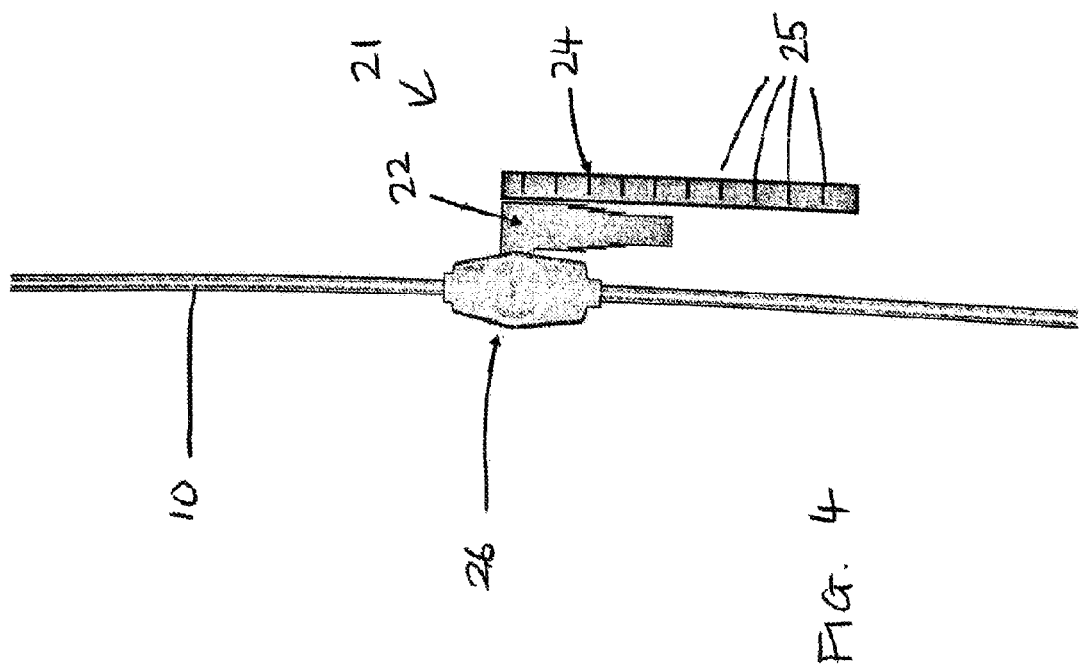
FIG. 4 is a schematic view of an apparatus according to a second embodiment of the disclosure.

FIG. 4 illustrates an alternative embodiment of the apparatus of the disclosure 21, shown connected to a shunt valve 26 on ventricular catheter 10 which forms part of a ventricular shunt. The apparatus 21 includes a distensible member 22 which is located adjacent to a scale 24. The distensible member 22 is a tube which is arranged such that it extends along the length of the scale 24 according to the pressure of the fluid in the apparatus 21. The scale 24 is marked with radiopaque markers 25. The distensible member 22 is made from or coated with a radiopaque material, for example silicone rubber, so that the length of the distensible member 22, relative to the scale 24 can be assessed from an X-ray image of the apparatus 21. The distensible member 22 is preferably fabricated from a material which regains its original shape and length when drained of fluid. To assess the CSF pressure an X-ray image of the apparatus is obtained, to enable medical professionals to determine the relative length of the distensible member 22 and hence gain an indication of the CSF pressure. FIG. 5a illustrates an apparatus 21 taking a measurement in a patient with low CSF pressure. The distensible member 22 extends only a small amount along the scale 24. FIG. 5b illustrates an apparatus 21 taking a measurement in a patient with normal CSF pressure. The distensible member 22 extends further along the scale 24. FIG. 5c illustrates an apparatus 21 taking a measurement in a patient with high CSF pressure. The distensible member 22 extends much further along the scale 24.

Figure 7A:
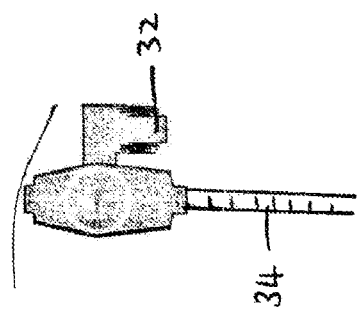
FIG. 7a is a schematic view of the apparatus of FIG. 6 measuring low pressure CSF.
Figure 7B:
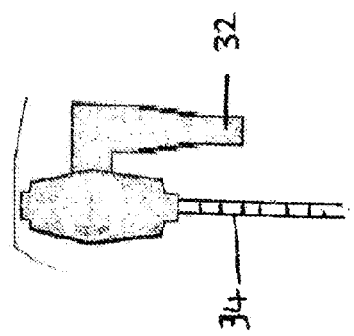
FIG. 7b is a schematic view of the apparatus of FIG. 6 measuring normal pressure CSF.
Figure 7C:
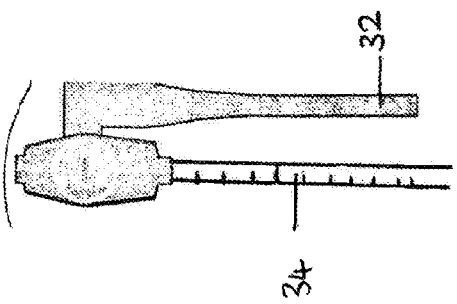
FIG. 7c is a schematic view of the apparatus of FIG. 6 measuring high pressure CSF.
Figure 6:
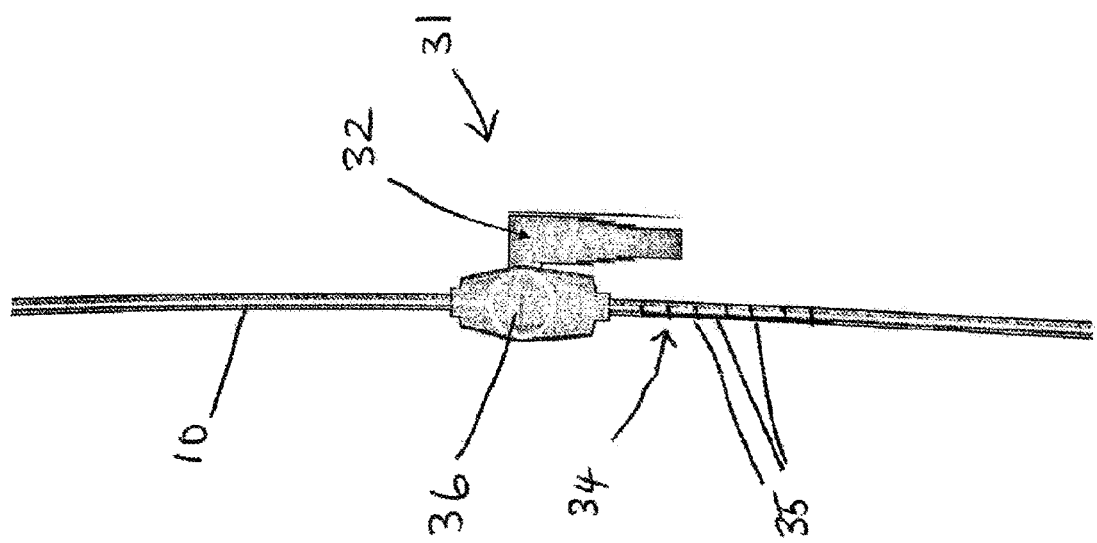
FIG. 6 is a schematic view of an apparatus according to a third embodiment of the disclosure.

FIG. 6 illustrates an alternative embodiment of the apparatus of the disclosure 31, shown connected to a shunt valve 36 on ventricular catheter 10 which forms part of a ventricular shunt. The apparatus 31 includes a distensible member 32 which is located adjacent to the ventricular catheter 10. The ventricular catheter 10 is provided with a scale 34. The distensible member 32 is a tube which is arranged such that it extends along the length of the scale 34 according to the pressure of the fluid in the apparatus 31. The scale 34 is marked with radiopaque markers 35. The distensible member 32 is made from or coated with a radiopaque material, for example silicone rubber, so that the length of the distensible member 32, relative to the scale 34 can be assessed from an X-ray image of the apparatus 31. The distensible member 32 is preferably fabricated from a material which regains its original shape and length when drained of fluid. To assess the CSF pressure an X-ray image of the apparatus is obtained, to enable medical professionals to assess the relative length of the distensible member 32 and hence gain an indication of the CSF pressure. FIG. 7a illustrates an apparatus 31 taking a measurement in a patient with low CSF pressure. The distensible member 32 extends only a small amount. FIG. 7b illustrates an apparatus 31 taking a measurement in a patient with normal CSF pressure. The distensible member 32 extends further along the scale 34. FIG. 75c illustrates an apparatus 31 taking a measurement in a patient with high CSF pressure. The distensible member 32 extends much further along the scale 24. The apparatus 31 is very similar to the apparatus 21 described in relation to FIGS. 5 and 6, the main difference being that the scale is located on the ventricular catheter 10, rather than being a separate element of the apparatus.

FIG. 8 illustrates an alternative embodiment of the apparatus of the disclosure 41, shown connected to a shunt valve 47 on ventricular catheter 10 which forms part of a ventricular shunt. The apparatus 41 includes a distensible member 42 which is located within an outer container 43. The outer container 43 is provided with a scale 44 marked with radiopaque markings 45. The end of the distensible member 42 is provided with a radiopaque marker 46. When CSF pressure increases the distensible member 42 extends along the length of the container 43. Both the end 46 of the distensible member 42 and the markings 45 on the scale 44 are either made from or coated with a radiopaque material. The outer container 43 is transparent to X-rays, and the location of the radiopaque marker 46, and hence the end of the distensible member 42, with respect to the scale 44 can be assessed from a simple X-ray image of the apparatus 41. The distensible member 42 is preferably fabricated from a material which regains its original shape and length when drained of fluid. To assess the CSF pressure an X-ray image of the apparatus 41 is obtained to enable medical professionals to determine the length of the distensible member 42 with respect to the scale 44 and hence determine the CSF pressure in the patient's shunt. FIG. 9a illustrates an apparatus 41 taking a measurement in a patient with low CSF pressure. The distensible member 42, and hence the radiopaque marker 46, extends only a small amount along the scale 44. FIG. 9b illustrates an apparatus 41 taking a measurement in a patient with normal CSF pressure. The distensible member 42, and hence the radiopaque marker 46, extends further along the scale 44. FIG. 9c illustrates an apparatus 41 taking a measurement in a patient with high CSF pressure. The distensible member 42, and hence the radiopaque marker 46, extends much further along the scale 44.

FIG. 10 illustrates an alternative embodiment of the apparatus of the disclosure 51, shown connected to a ventricular catheter 10 which forms part of a ventricular shunt, at a location upstream of the shunt valve 57. The apparatus 51 includes a distensible member 52 which is located adjacent to a scale 54. The apparatus 51 also includes a bladder 53 and a piston 56 (see FIGS. 11A-11C) which is connected to both the distensible member 52 and the bladder 53. The components of the apparatus 51 are arranged such that an increase in CSF pressure causes the bladder 53 to distend, which then in turn acts upon the piston 56, causing the distensible member 52 to extend along the length of the scale 54. The scale 54 is marked with radiopaque markers 55 and the distensible member 52 is made from or coated with a radiopaque material, for example silicone rubber, so that the length of the distensible member 52, relative to the scale 54 can be assessed from an X-ray image of the apparatus 51. The distensible member 52 is preferably fabricated from a material which regains its original shape and length when drained of fluid. To assess the CSF pressure an X-ray image of the apparatus 51 is obtained, which enables medical professionals to determine the relative length of the distensible member 52 and hence gain an indication of the CSF pressure. FIG. 11a illustrates an apparatus 51 taking a measurement in a patient with low CSF pressure. The apparatus 51 is illustrated with the distensible member in cross-section to show the piston 56 located therewithin. At low CSF pressure the bladder 53 is distended only a small amount, and the piston 56 is moved only a small amount, causing distensible member 52 to extend only a small amount along the scale 54. FIG. 11b illustrates an apparatus 51 taking a measurement in a patient with normal CSF pressure. The bladder 53 is distended further than seen in FIG. 11a, hence piston 56 has been moved further, causing distensible member 52 to extend further along the scale 54. FIG. 11c illustrates an apparatus 51 taking a measurement in a patient with high CSF pressure. The bladder 53 is distended much further, hence piston 56 has been moved much further, causing distensible member 52 extend much further along the scale 54. The piston 56 may be spring biased into the low CSF pressure position illustrated in FIG. 11a such that the distensible member 52 returns to its unextended form when the shunt is drained of fluid.

The apparatus of the disclosure allows CSF pressure in a cerebral shunt to be easily determined following a simple and un-invasive X-ray procedure, exposing the patient to a far lower dose of radiation.

The invention claimed is:

1. An apparatus for measuring pressure of cerebrospinal fluid in a ventricular shunt implanted in a patient, the apparatus comprising:
   a distensible member and a graduated scale, both the distensible member and the graduated scale comprising radiopaque markers, wherein the distensible member is arranged adjacent to the graduated scale such that a length of the distensible member relative to the graduated scale can be assessed from an X-ray image of the apparatus,
   wherein the distensible member and the graduated scale are configured and arranged so that cerebrospinal fluid in the ventricular shunt at least partially fills an interior chamber defined by the distensible member so as to cause the distensible member to distend in the direction of the graduated scale, and
   wherein the apparatus is attachable to, or incorporated into, the ventricular shunt at a location either at or upstream of a shunt valve forming part of the ventricular shunt.

2. An apparatus according to claim 1, wherein the distensible member is fabricated from a radiopaque material.

3. An apparatus according to claim 1, wherein the distensible member comprises distensible tubing.

4. An apparatus according to claim 1, wherein the ventricular shunt comprises a ventricular catheter and the apparatus is attachable to the ventricular catheter.

5. An apparatus according to claim 4, wherein the graduated scale is located on the ventricular catheter.

6. An implantable ventricular shunt comprising a ventricular catheter, a shunt valve connected to the ventricular catheter, a further catheter connected to the shunt valve, and apparatus for measuring pressure in the ventricular catheter, the apparatus for measuring pressure in the ventricular shunt comprising:
   a distensible member and a graduated scale, both the distensible member and the graduated scale comprising radiopaque markers, wherein the distensible member is arranged adjacent to the graduated scale such that a length of the distensible member relative to the graduated scale can be assessed from an X-ray image of the apparatus,
   wherein the distensible member and the graduated scale are configured and arranged so that cerebrospinal fluid in the ventricular shunt is in direct contact with, and acts directly on, a distensible material that makes up the distensible member and at least partially fills an interior chamber defined by the distensible member and the distensible member is distensible in the direction of the graduated scale, and wherein the apparatus for measuring pressure in the ventricular shunt is attachable to, or incorporated into, the ventricular shunt at a location either at or upstream of the shunt valve.

7. An apparatus for measuring pressure of cerebrospinal fluid in a ventricular shunt implanted in a patient, the apparatus comprising:

a distensible member and a graduated scale, both the distensible member and the graduated scale comprising radiopaque markers, wherein the distensible member is arranged adjacent to the graduated scale such that a length of the distensible member relative to the graduated scale can be assessed from an X-ray image of the apparatus, wherein the distensible member and the graduated scale are configured and arranged so that cerebrospinal fluid in the ventricular shunt is in direct contact with, and acts directly on, a distensible material that makes up the distensible member and at least partially fills an interior chamber defined by the distensible member and the distensible member is distensible in the direction of the graduated scale, and wherein the apparatus is attachable to, or incorporated into, the ventricular shunt at a location either at or upstream of a shunt valve forming part of the ventricular shunt.

8. An apparatus according to claim 7, wherein the distensible member is fabricated from a radiopaque material.

9. An apparatus according to claim 7, wherein the distensible member comprises distensible tubing.

10. An apparatus according to claim 7, wherein the ventricular shunt comprises a ventricular catheter and the apparatus is attachable to the ventricular catheter.

11. An apparatus according to claim 10, wherein the graduated scale is located on the ventricular catheter.

* * * * *